United States Patent [19]

Rosenblum

[11] Patent Number: 5,230,694
[45] Date of Patent: Jul. 27, 1993

[54] UROLOGICAL PROSTHESIS

[76] Inventor: Jeffrey L. Rosenblum, 180 Barlow Dr. South, Brooklyn, N.Y. 11234

[21] Appl. No.: 818,791

[22] Filed: Jan. 9, 1992

[51] Int. Cl.$^5$ ............................................. A61F 2/26
[52] U.S. Cl. ........................................ 600/40; 623/11
[58] Field of Search ................................. 600/39–41; 623/11, 66

[56] References Cited

U.S. PATENT DOCUMENTS

| | | |
|---|---|---|
| 4,005,699 | 2/1977 | Bucalo . |
| 4,151,840 | 5/1979 | Barrington . |
| 4,151,841 | 5/1979 | Barrington . |
| 4,187,839 | 2/1980 | Nuwayer . |
| 4,318,396 | 3/1982 | Finney . |
| 4,342,308 | 8/1982 | Trick . |
| 4,378,792 | 4/1983 | Finney . |
| 4,411,261 | 10/1983 | Finney . |
| 4,517,967 | 5/1985 | Timm . |
| 4,522,198 | 6/1985 | Timm et al. ................ 600/40 |
| 4,541,420 | 9/1985 | Timm . |
| 4,545,081 | 10/1985 | Nestor . |
| 4,611,584 | 9/1986 | Finney . |
| 4,619,251 | 10/1986 | Helms . |
| 4,669,456 | 6/1987 | Masters ....................... 600/40 |
| 4,693,719 | 9/1987 | Franko . |
| 4,790,298 | 12/1988 | Trick . |
| 4,791,917 | 12/1988 | Finney . |
| 4,807,608 | 2/1989 | Levius . |
| 4,875,472 | 10/1989 | Levius ......................... 600/40 |
| 4,881,531 | 11/1989 | Timm . |
| 5,050,592 | 9/1991 | Olmedo . |
| 5,063,914 | 11/1991 | Cowen . |
| 5,129,880 | 7/1992 | Grundei ....................... 600/40 |

OTHER PUBLICATIONS

R. T. Bergman et al., "Plastic Reconstruction of the Penis," *J. Urol.*, vol. 59, pp. 1174–1182 (1948).
R. Hrebinko et al., "Early Experience with the Duraphase Penile Prosthesis," *J. Urol.*, vol. 143, pp. 60–61 (1990).
J. N. Kabalin et al., "Infectious Complications of Penile Prosthesis Surgery," *J. Urol.*, vol. 139, pp. 953–955 (1988).
J. J. Kaufman et al., "Complications of Penile Prosthesis Surgery for Impotence," *J. Urol.*, vol. 128, pp. 1192–1194 (1982).
R. Kessler, "Complications of Inflatable Penile Prostheses," *Urology*, vol. 18, pp. 470–472 (1981).
J. N. Krieger et al., "Size Considerations for Custom Penile Prostheses," *J. Urol.*, vol. 144, pp. 1482–1483 (1990).
K. Levinson et al., "Omniphase Penile Prosthesis: Delayed Bilateral Central Cable Breakage," *J. Urol.*, vol. 141, pp. 618–619 (1989).
J. J. Mulcahy et al., "Duraphase Penile Prosthesis—Results of Clinical Trials in 63 Patients," *J. Urol.*, vol. 143, pp. 518–519 (1990).
J. J. Mulcahy, "The Self-Contained Inflatable and Mechanical Penile Prosthesis," AUA Update Series, vol. 6, lesson 20 (1987).

(List continued on next page.)

*Primary Examiner*—Randall L. Green
*Assistant Examiner*—Gina M. Gualtieri
*Attorney, Agent, or Firm*—Bryan Cave

[57] ABSTRACT

A manually operable mechanical penile implant for overcoming the effects of male erectile impotence is disclosed. The implant has an elongate housing containing an elongate coil and stop means located between the two ends of the housing. Many or most of the coil turns are normally located between the stop means and the near (or proximal) end of the housing. When the device is to be used, the coil turns are drawn past the stop means toward the far (or distal) end of the housing and are locked between that end and the stop means, thereby providing rigidity (and in preferred embodiments, additional length) to the housing and therefore to the corpus cavernosum in which the device is located. In contrast to known mechanical (i.e., non-fluidic) implants, in preferred embodiments the implant may be significantly increased in length for use and significantly decreased in length after use. In contrast to fluidic devices, there is no fluid to leak or any pump or valve to be replaced in case of malfunction.

44 Claims, 8 Drawing Sheets

OTHER PUBLICATIONS

P. W. Nadig et al., "Noninvasive Device to Produce and Maintain an Erection-Like State," *Urology*, vol. 17, pp. 126–131 (1986).

J. E. Oesterling, "A Simple Technique for Removal of Eroded Penile Prostheses," *J. Urol.*, vol. 142, pp. 1538–1539 (1989).

E. A. Tanagho et al., (eds.), *Contemporary Management of Impotence and Infertility*, pp. 191–200 (1988).

P. C. Walsh et al. (eds.), *Campbell's Urology*, vol. 1, pp. 700–735 (5th ed., 1986).

S. K. Wilson et al., "Eleven Years of Experience with the Inflatable Penile Prostheses," *J. Urol.*, vol. 139, pp. 951–952 (1988).

R. Witherington, "Vacuum Constriction Device for Management of Erectile Impotence," *J. Urol.*, vol. 141, pp. 320–322 (1989).

Mentor Corporation brochure, "Vacuum Constriction Devices," 2 pages (Jun. 1990).

Mentor Corporation brochure, "ACU-FORM TM Penile Prosthesis," 2 pages (May 1991).

Mentor Corporation brochure, "Malleable Penile Prosthesis," 2 pages (Nov. 1990).

Mentor Corporation brochure, "Mark II Inflatable Penile Prosthesis," 2 pages (May 1990).

Mentor Corporation brochure, "Mark II Inflatable Penile Prosthesis," 2 pages (Jan. 1991).

Mentor Corporation brochure, "ALPHA I ®0 Inflatable Penile Prosthesis," 2 pages (May 1991).

American Medical Systems brochure, "Dynaflex—Fit for Performance: A Review of the Results and Mechanics of the Dynaflex TM Penile Prosthesis," 3 pages (1990).

American Medical Systems brochure, "700 UL-TREX TM Penile Prosthesis," 4 pages (1990).

American Medical Systems brochure, "A Brief Guide to Your Choices for Impotence Treatment," 4 pages (1989).

Osborn Medical Systems brochure, "Impotence—The Non-Surgical Solution," 2 pages (1989).

Osborn Medical Systems brochure, "Impotence—When you want a non-surgical solution, there's only one ...," 4 pages (1990).

American Medical Systems brochure, "AMS 700 CX TM Inflatable Penile Prosthesis," 2 pages (1988).

Brochure for Third Edition of *Urogynecology and Urodynamics: Theory and Practice* by D. R. Ostergard et al., 2 pages (no date).

Medical Engineering Corp. poster, "SURGITEK—Innovators Not Imitators" (1988).

F. Hinman, Jr., *Atlas of Urologic Surgery*, pp. 103–116 (1989).

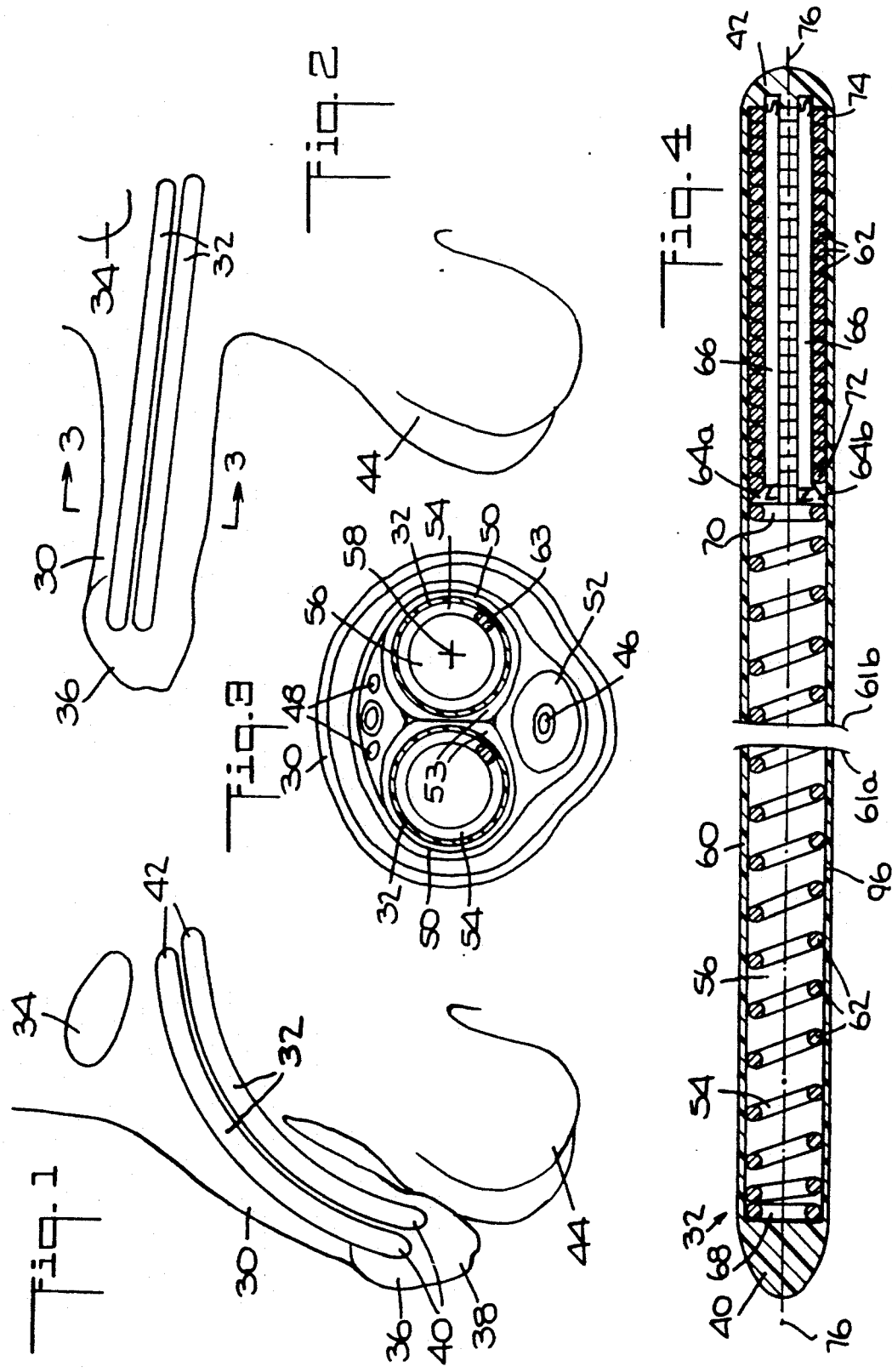

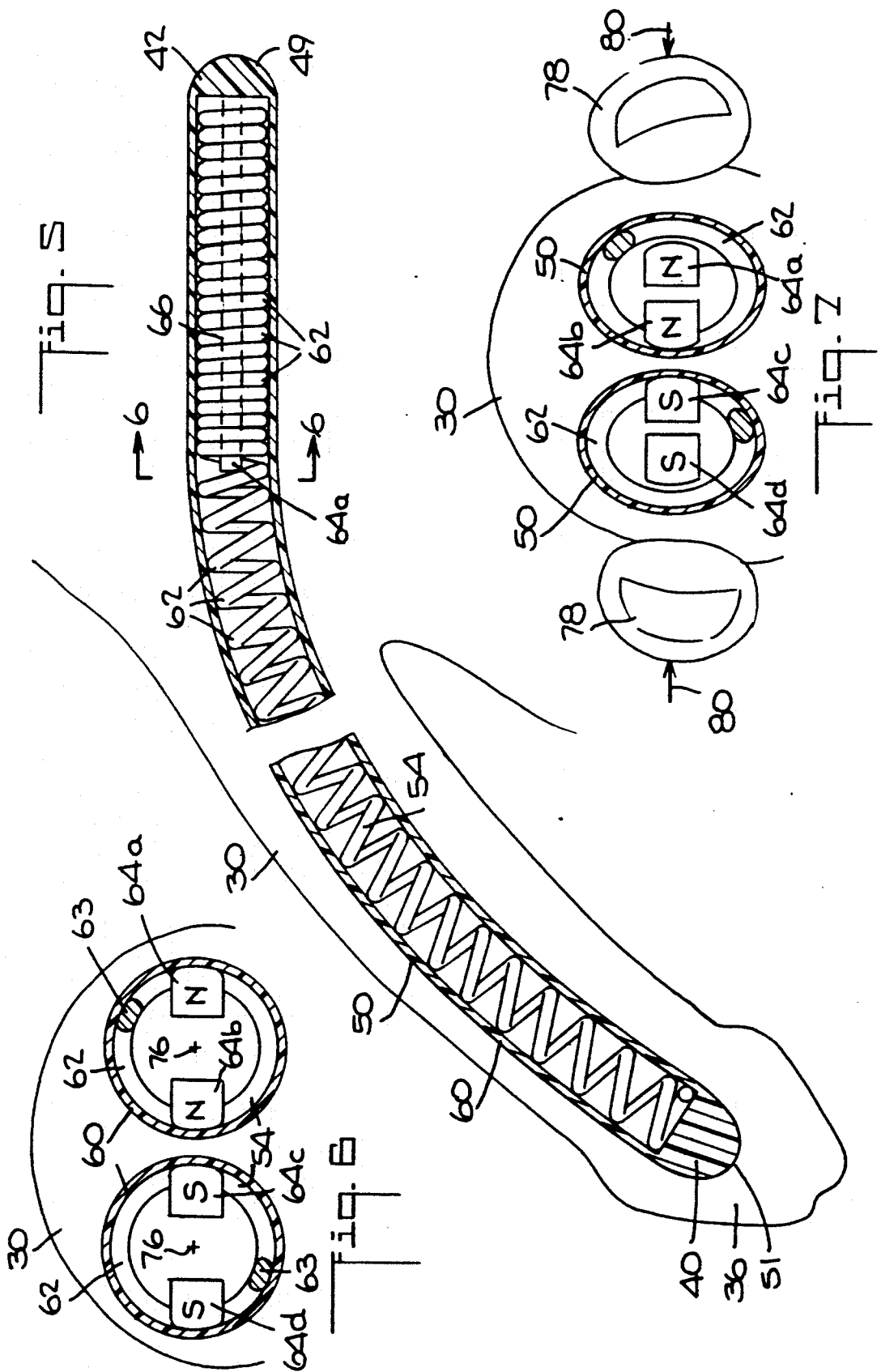

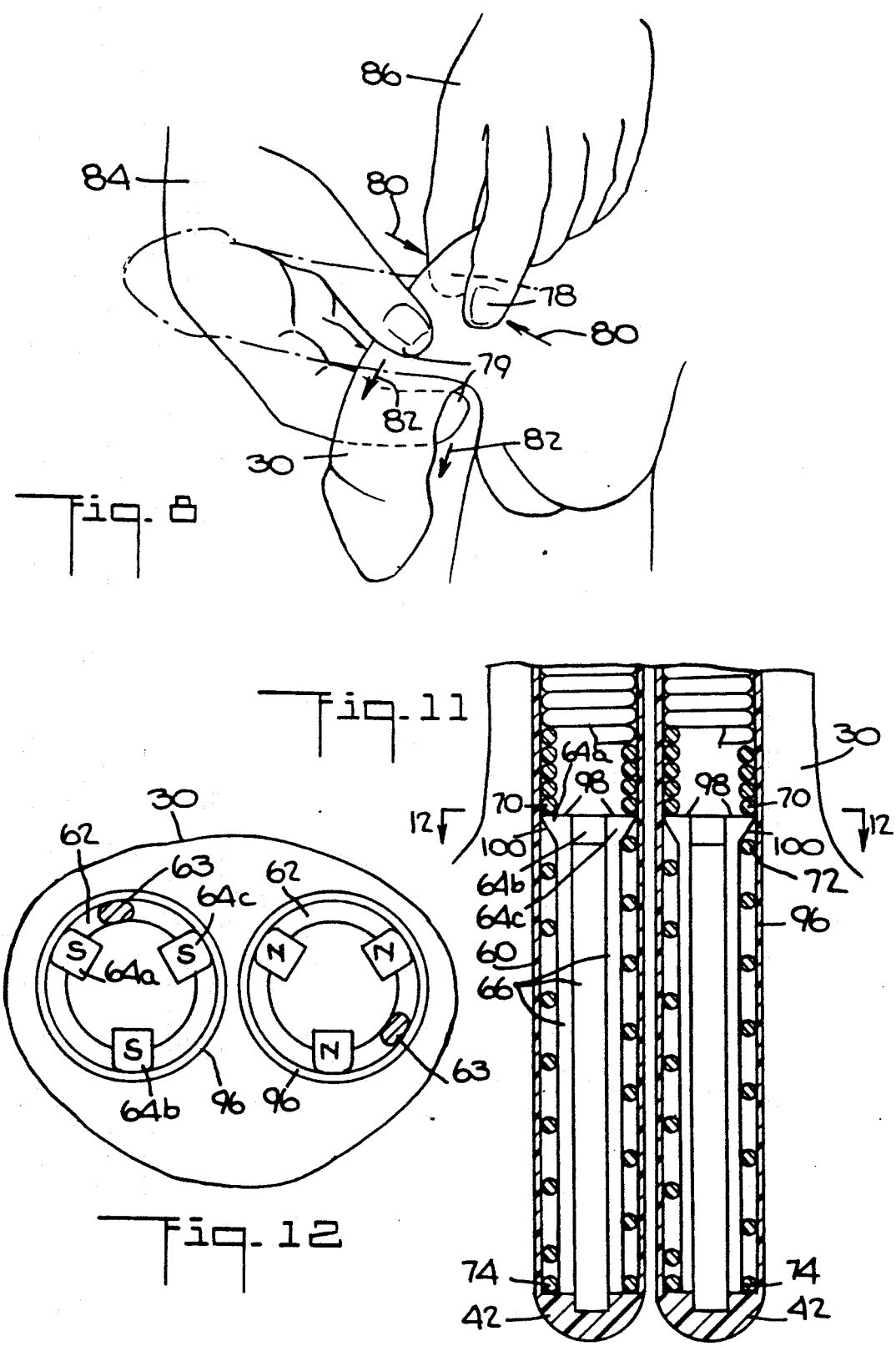

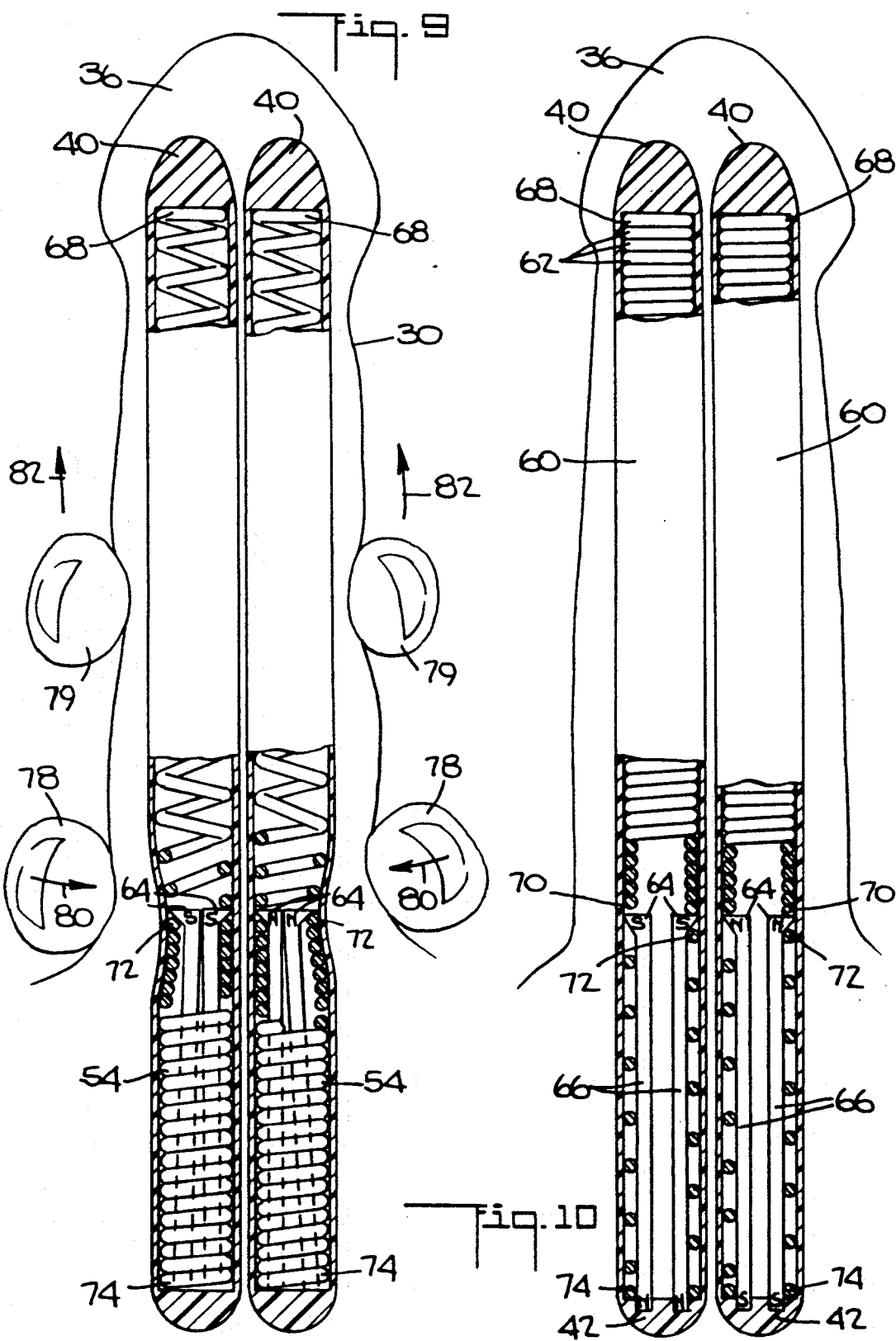

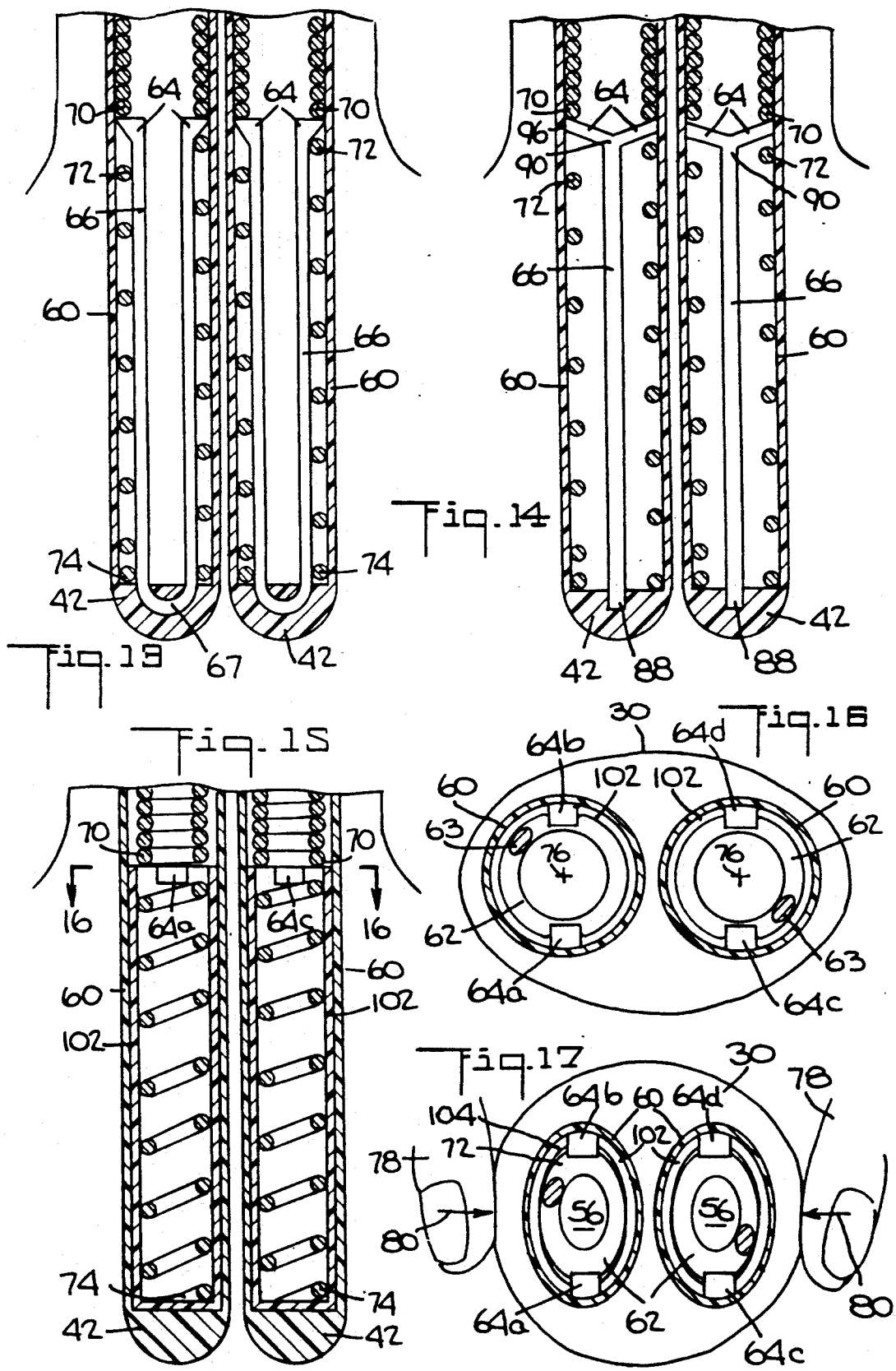

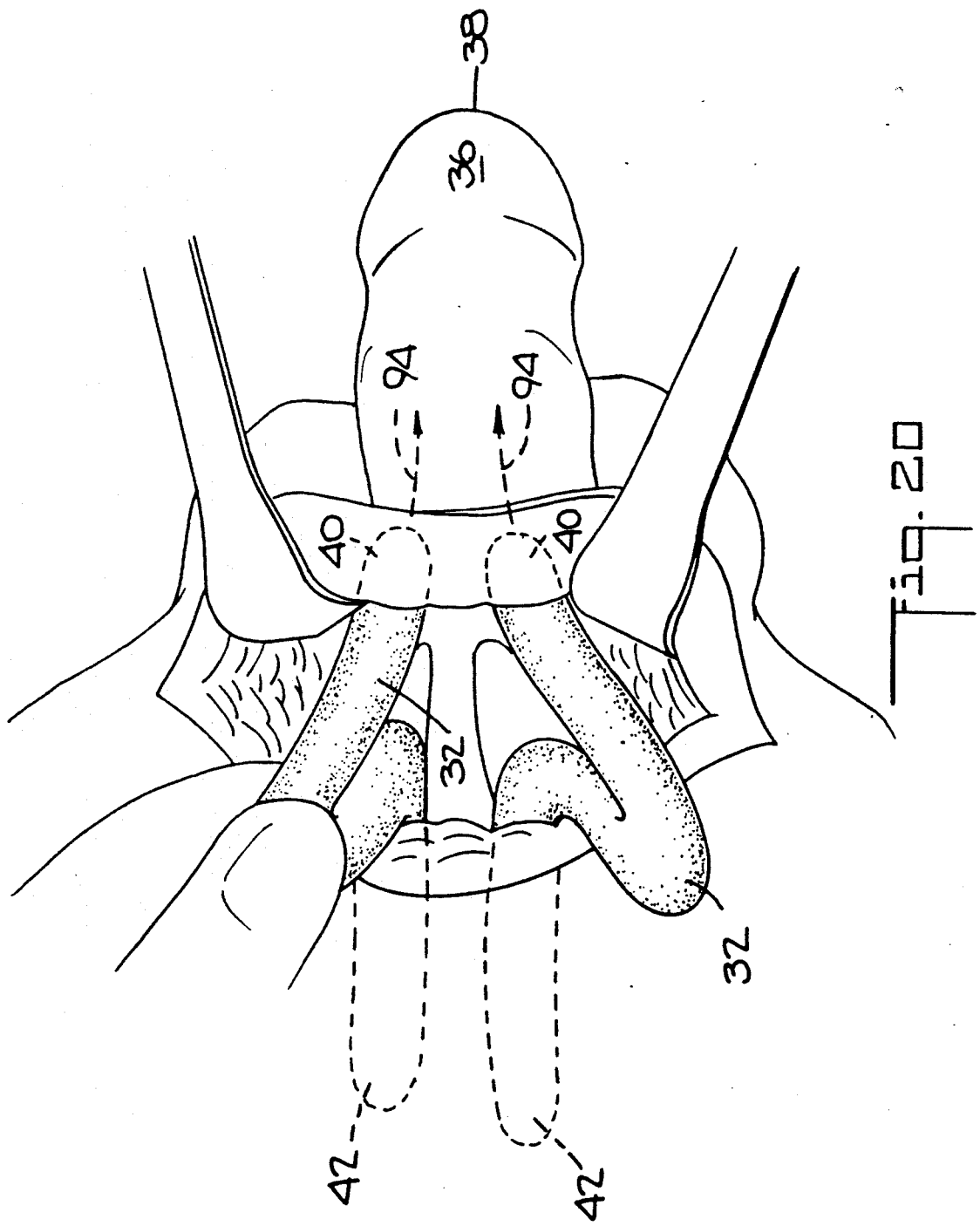

UROLOGICAL PROSTHESIS

BACKGROUND OF THE INVENTION

This invention relates to the field of medical prostheses, particularly to the field of urological prostheses, and more particularly to the field of penile implants.

There are numerous physiological causes of male impotence. For example, diseases such as diabetes and multiple sclerosis and trauma caused by injury or surgery can damage nerves or blood vessels that are necessary for tumescence. Drugs and advanced age may also cause impotence.

Numerous external devices (e.g., vacuum systems) and internal devices have been proposed to overcome impotence so that an erection can be achieved and maintained. Various surgical techniques for implanting such internal devices have become wellknown. Internal and external devices for dealing with impotence, surgical techniques for implanting such internal devices, and other urological prostheses are disclosed in U.S. Pat. Nos. 5,063,914, 5,050,592, 4,881,531, 4,875,472, 4,807,608, 4,791,917, 4,790,298, 4,693,719, 4,669,456, 4,619,251, 4,611,584, 4,545,081, 4,541,420, 4,522,198, 4,517,967, 4,411,261, 4,378,792, 4,342,308, 4,318,396, 4,187,839, 4,151,841, 4,151,840, 4,005,699; and in R. T. Bergman et al., "Plastic Reconstruction of the Penis," *J. Urol.*, vol. 59, pp. 1174-1182 (1948); R. Hrebinko et al., "Early Experience with the Duraphase Penile Prosthesis," *J. Urol.*, vol. 143, pp. 60-61 (1990); J. N. Kabalin et al., "Infectious Complications of Penile Prosthesis Surgery," *J. Urol.*, vol. 139, pp. 953-955 (1988); J. J. Kaufman et al., "Complications of Penile Prosthesis Surgery for Impotence," *J. Urol.*, vol. 128, pp. 1192-1194 (1982); R. Kessler, "Complications of Inflatable Penile Prostheses," *Urology*, vol. 18, pp. 470-472 (1981); J. N. Krieger et al., "Size Considerations for Custom Penile Prostheses," *J. Urol.*, vol. 144, pp. 1482-1483 (1990); K. Levinson et al., "Omniphase Penile Prosthesis: Delayed Bilateral Central Cable Breakage," *J. Urol.*, vol. 141, pp. 618-619 (1989); J. J. Mulcahy et al., "Duraphase Penile Prosthesis— Results of Clinical Trials in 63 Patients," *J. Urol.*, vol. 143, pp. 518-519 (1990); J. J. Mulcahy, "The Self-Contained Inflatable and Mechanical Penile Prosthesis," *AUA Update Series*, vol. 6, lesson 20 (1987); P. W. Nadig et al., "Noninvasive Device to Produce and Maintain an Erection-Like State," *Urology*, vol. 17, pp. 126-131 (1986); J. E. Oesterling, "A Simple Technique for Removal of Eroded Penile Prostheses," *J. Urol.*, vol. 142, pp. 1538-1539 (1989); E. A. Tanagho et al. (eds.), *Contemporary Management of Impotence and Infertility*, pp. 191-200 (1988); P. C. Walsh et al. (eds.), *Campbell's Urology*, vol 1, pp. 700-735 (5th ed., 1986); S. K. Wilson et al., "Eleven Years of Experience with the Inflatable Penile Prosthesis," *J. Urol.*, vol. 139, pp. 951-952 (1988); R. Witherington, "Vacuum Constriction Device for Management of Erectile Impotence," *J. Urol.*, Vol. 141, pp. 320-322 (1989); Mentor Corporation brochure, "Vacuum Constriction Devices," 2 pages (June 1990); Mentor Corporation brochure, "ACU-FORM TM Penile Prosthesis," 2 pages (May 1991); Mentor Corporation brochure, "Malleable Penile Prosthesis," 2 pages (November 1990); Mentor Corporation brochure, "Mark II Inflatable Penile Prosthesis," 2 pages (May 1990); Mentor Corporation brochure, "Mark II Inflatable Penile Prosthesis," 2 pages (January 1991); Mentor Corporation brochure, "ALPHA I ® Inflatable Penile Prosthesis," 2 pages (May 1991); American Medical Systems brochure, "Dynaflex— Fit for Performance: A Review of the Results and Mechanics of the Dynaflex TM Penile Prosthesis," 3 pages (1990); American Medical Systems brochure, "700 ULTREX TM Penile Prosthesis," 4 pages (1990); American Medical Systems brochure, "A Brief Guide to Your Choices for Impotence Treatment," 4 pages (1989); Osborn Medical Systems brochure, "Impotence— The Non-Surgical Solution," 2 pages (1989); Osborn Medical Systems brochure, "Impotence— When you want a non-surgical solution, there's only one ... ," 4 pages (1990); American Medical Systems brochure, "AMS 700 CX TM Inflatable Penile Prosthesis," 2 pages (1988); Brochure for Third Edition of *Urogynecology and Urodynamics: Theory and Practice* by D. R. Ostergard et al., 2 pages (no date); Medical Engineering Corp. poster, "SURGITEK— Innovators Not Imitators" (1988); and F. Hinman, Jr., *Atlas of Urologic Surgery*, pp. 103-116 (1989).

The use of coils (usually in the form of springs) in penile implants is disclosed in some of those documents. See, e.g., U.S. Pat. Nos. 5,063,914, 4,881,531, 4,875,472, 4,807,608, 4,790,298, 4,693,719, 4,669,456, 4,619,251, 4,545,081, 4,541,420, 4,522,198, 4,517,967, 4,342,308, 4,187,839, and Mentor Corporation brochure, "Malleable Penile Prosthesis," 2 pages (November 1990). The use of magnets in penile implants is disclosed in some of those documents. See, e.g., U.S. Pat. Nos. 4,791,917, 4,411,261, 4,378,792, 4,342,308, 4,318,396, and 4,005,699. U.S. Pat. No. 4,342,308 uses both magnets and springs. Squeezing the outside of the device (after implantation) to activate and/or deactivate it is disclosed in some of those documents, e.g., U.S. Pat. No. 4,875,472; E. A. Tanagho et al. (eds.), *Contemporary Management of Impotence and Infertility*, p. 198 (1988); and American Medical Systems brochure, "Dynaflex— Fit for Performance: A Review of the Results and Mechanics of the Dynaflex TM Penile Prosthesis," 3 pages (1990). Use of a constriction band is disclosed in some of those documents, e.g., R. Witherington, "Vacuum Constriction Device for Management of Erectile Impotence," *J. Urol.*, vol. 141, pp. 320-322 (1989).

All of the documents identified in this application, including all of the foregoing, are incorporated by reference herein in their entirety for all purposes.

The devices used internally are surgically implanted in the corpora cavernosa (one device or part of a two-housing device in each corpus cavernosum) and typically have biocompatible material on their outer surfaces. One class of device pressurizes fluid to expand and rigidify the device, which in turn rigidifies each of the corpora cavernosa and, therefore, the penis. These devices have the advantage of more closely simulating nature (by allowing movement between flaccid and erect states) than the older devices that contain a solid relatively inflexible elongate bar of material within each housing. Those devices not using fluid include the previously mentioned devices containing a solid relatively inflexible rod or bar, devices containing an elongate malleable rod or bar, and devices containing an articulated or segmented elongate member. Such devices are disclosed in the above-identified documents, and all of these devices have their disadvantages.

The drawbacks of the pressurized fluid devices include possible fluid leakage and pump and valve failure, any of which typically necessitates corrective surgery.

The drawbacks of the inflexible rod, flexible rod, and articulated devices are also well-known and usually include the inability to be reduced in length to any significant extent when not in use and the resulting poor concealability.

Accordingly, there is a continuing need for penile implants that avoid the problems of the fluid devices and also avoid the problems of the known non-fluid devices.

SUMMARY OF THE INVENTION

A penile implant satisfying that need and avoiding those problems has now been developed. The implant is manually operable and may be used to overcome the effects of male erectile impotence. The implant has a flexible elongate housing containing an elongate coil and stop means located between the two ends of the housing. Many or most of the coil turns are normally located between the stop means and the near (or proximal) end of the housing. When the device is to be used, coil turns are drawn past the stop means toward the far (or distal) end of the housing and are locked between that end and the stop means, thereby providing rigidity, and in preferred embodiments additional length, to the housing and therefore to the corpus cavernosum in which the device is located. One such device is implanted in each of the two corpora cavernosa.

In contrast to known mechanical (i.e., non-fluidic) implants, in preferred embodiments the implant may be significantly increased in length for use and significantly decreased in length after use, thereby more nearly mimicking natural biological functioning. In contrast to fluidic devices, there is no fluid to leak or any pump or valve to be replaced in case of malfunction. Furthermore, activation (rigidification and, in preferred embodiments, lengthening) of the device can form a more natural and less obtrusive part of foreplay than the activation schemes required by known devices. Other features and advantages of the invention will be apparent to those skilled in the art.

Broadly, the device of this invention is an implantable penile prosthesis which is changeable from a less rigid configuration to a more rigid configuration, which is temporarily lockable in the more rigid configuration, and which when located in the corpus cavernosum and locked in the more rigid configuration helps to maintain the corpus cavernosum in a more rigid configuration; the corpus cavernosum having a proximal end, which is nearer the symphysis pubis, and a distal end, which is farther from the symphysis pubis; said prosthesis comprising:

(a) a flexible elongate housing having a lateral wall, a longitudinal axis, a proximal end, and a distal end, the proximal end of the housing being adapted to be located closer to the proximal end of the corpus cavernosum and the distal end of the housing being adapted to be located closer to the distal end of the corpus cavernosum when the prosthesis is located in the corpus cavernosum, the prosthesis being in a less rigid configuration when the housing is in a less rigid configuration and being in a more rigid configuration when the housing is in a more rigid configuration;

(b) an elongate coil inside the housing and comprising a plurality of turns, the coil having a distal end and a proximal end, the distal end of the coil being located toward the distal end of the housing and the proximal end of the coil being located toward the proximal end of the housing;

(c) temporary locking means located between the distal and proximal ends of the housing, a plurality of coil turns normally being located between the proximal end of the housing and the temporary locking means when the housing is in a less rigid configuration, the temporary locking means being designed (i) to permit at least one of the coil turns located between the proximal end of the housing and the temporary locking means to be moved to a location between the temporary locking means and the distal end of the housing and (ii) to temporarily lock the coil turns located between the temporary locking means and the distal end of the housing so that they cannot be moved back to their normal location between the proximal end of the housing and the temporary locking means until the temporary locking means is unlocked;

the coil, temporary locking means, and housing being designed so that when a sufficient number of coil turns have been moved from their normal location between the temporary locking means and the proximal end of the housing to a position between the temporary locking means and the distal end of the housing and temporarily locked there, the housing is temporarily locked in a more rigid configuration, thereby temporarily locking the prosthesis in a more rigid configuration and thereby locking the corpus cavernosum in a more rigid configuration.

In another aspect, the device of the present invention is an implantable manually operable penile prosthesis which is elongatable from a less extended configuration to a more extended configuration, which is temporarily lockable in the more extended configuration, and which when located in the corpus cavernosum and locked in the more extended configuration helps to maintain the corpus cavernosum in a more extended configuration; the corpus cavernosum having a proximal end, which is nearer the symphysis pubis, and a distal end, which is farther from the symphysis pubis; said prosthesis comprising:

(a) an elongatable housing having a lateral wall, a longitudinal axis, a proximal end, and a distal end, the proximal end of the housing being adapted to be located closer to the proximal end of the corpus cavernosum and the distal end of the housing being adapted to be located closer to the distal end of the corpus cavernosum when the prosthesis is located in the corpus cavernosum, the prosthesis being in a less extended configuration when the housing is in a less extended configuration and being in a more extended configuration when the housing is in a more extended configuration;

(b) an elongate coil inside the housing and comprising a plurality of turns, the coil having a distal end and a proximal end, the distal end of the coil being located toward the distal end of the housing and the proximal end of the coil being located toward the proximal end of the housing;

(c) manually operable temporary locking means located between the distal and proximal ends of the housing, a plurality of coil turns normally being located between the proximal end of the housing and the temporary locking means when the housing is in a less extended configuration, the temporary locking means being designed (i) to permit at least one of the coil turns located between the proximal end of the housing and the temporary locking means to be manually moved to a location between the temporary locking means and the distal end of the housing and (ii) to temporarily lock the coil turns located between the temporary locking means and the distal end of the housing so that they cannot be moved back to their normal location between the proximal end of the housing and the temporary locking means until the temporary locking means is manually unlocked;

the coil, temporary locking means, and housing being designed so that when a sufficient number of coil turns have been moved from their normal location between the temporary locking means and the proximal end of the housing to a position between the temporary locking means and the distal end of the housing and temporarily locked there, the housing is temporarily locked in a more extended configuration, thereby temporarily locking the prosthesis in a more extended configuration and thereby locking the corpus cavernosum in a more extended configuration.

Another aspect of the invention relates to an implantable manually operable penile prosthesis which is elongatable from a less extended configuration to a more extended configuration, which is temporarily lockable in the more extended configuration, and which when located in the corpus cavernosum and locked in the more extended configuration helps to maintain the corpus cavernosum in a more extended configuration; the corpus cavernosum having a proximal end, which is nearer the symphysis pubis, and a distal end, which is farther from the symphysis pubis; said prosthesis comprising:

(a) an elongate elongatable housing having a lateral wall, a longitudinal axis, a proximal end, and a distal end, the proximal end of the housing being adapted to be located closer to the proximal end of the corpus cavernosum and the distal end of the housing being adapted to be located closer to the distal end of the corpus cavernosum when the prosthesis is located in the corpus cavernosum, the prosthesis being in a less extended configuration when the housing is in a less extended configuration and being in a more extended configuration when the housing is in a more extended configuration;

(b) an elongate elongatable coil inside the housing and comprising a plurality of turns, the coil having a distal end and a proximal end, the distal end of the coil being located toward the distal end of the housing and the proximal end of the coil being located toward the proximal end of the housing, the turns of the coil also defining an elongate passageway centrally located in the coil and having a longitudinal axis, the longitudinal axis of the passageway roughly corresponding to the longitudinal axis of the housing;

(c) manually operable temporary locking means located between the distal and proximal ends of the housing, a plurality of coil turns normally being located between the proximal end of the housing and the temporary locking means when the housing is in a less extended configuration, the temporary locking means being designed (i) to permit at least one of the coil turns located between the proximal end of the housing and the temporary locking means to be manually moved to a location between the temporary locking means and the distal end of the housing and (ii) to temporarily lock the coil turns located between the temporary locking means and the distal end of the housing so that they cannot be moved back to their normal location between the proximal end of the housing and the temporary locking means until the temporary locking means is manually unlocked;

the coil, temporary locking means, and housing being designed so that when a sufficient number of coil turns have been moved from their normal location between the temporary locking means and the proximal end of the housing to a position between the temporary locking means and the distal end of the housing and temporarily locked there, the housing is temporarily locked in a more extended configuration, thereby temporarily locking the prosthesis in a more extended configuration and thereby locking the corpus cavernosum in a more extended configuration.

One preferred embodiment of the present invention is an implantable manually operable penile prosthesis which is elongatable from a less extended configuration to a more extended configuration, which is temporarily lockable in the more extended configuration, and which when located in the corpus cavernosum and locked in the more extended configuration helps to maintain the corpus cavernosum in a more extended configuration; the corpus cavernosum having a proximal end, which is nearer the symphysis pubis, and a distal end, which is farther from the symphysis pubis; said prosthesis comprising:

(a) an elongate elongatable housing having a lateral wall, a longitudinal axis, a proximal end, and a distal end, the proximal end of the housing being adapted to be located closer to the proximal end of the corpus cavernosum and the distal end of the housing being adapted to be located closer to the distal end of the corpus cavernosum when the prosthesis is located in the corpus cavernosum, the prosthesis being in a less extended configuration when the housing is in a less extended configuration and being in a more extended configuration when the housing is in a more extended configuration;

(b) an elongate elongatable coil inside the housing and comprising a plurality of turns, the coil having a distal end and a proximal end, the distal end of the coil being located toward the distal end of the housing and the proximal end of the coil being located toward the proximal end of the housing, the turns of the coil also defining an elongate passageway centrally located in the coil and having a longitudinal axis, the longitudinal axis of the passageway roughly corresponding to the longitudinal axis of the housing;

(c) a plurality of members in the housing, each member having a proximal end and a distal end, the members being located at least partially within the elongate passageway of the coil and being shorter than the elongate passageway, the proximal ends of the members being closer to the proximal end of the housing and the distal ends of the members being farther from the proximal end of the housing, the distal ends of the members being laterally movable towards and away from each other, a plurality of coil turns normally being located between the proximal end of the housing and the distal ends of the members when the housing is in a less extended configuration;

(d) stop means connected to the members near the distal ends of the members so that the stop means are movable laterally towards and away from each other, the stop means being normally biased away from each other towards the lateral wall of the housing but being sufficiently manually movable towards each other, when so stressed, to permit at least one of the plurality of coil turns located between the proximal end of the housing and the distal ends of the members to be manually moved to a location between the distal ends of the members and the distal ends of the housing, and when not so stressed, the normal bias moving the stop means far enough apart towards the lateral wall of the housing to temporarily lock the coil turns located between the distal ends of the members and the distal end of the housing so that they cannot be moved back to their normal location between the proximal end of the housing and the distal ends of the members until the stop means are manually moved towards each other;

the coil, members, stop means, and housing being designed so that when a sufficient number of coil turns have been moved from their normal location between the distal ends of the members and the proximal end of the housing to a position between the distal ends of the members and the distal end of the housing and temporarily locked there, the housing is temporarily locked in a more extended configuration, thereby temporarily locking the prosthesis in a more extended configuration and thereby locking the corpus cavernosum in a more extended configuration.

In preferred embodiments, the stop means are normally biased away from each other by magnetic repulsive force, which force is apparent when the ends of two or more bar magnets having the same polarity are brought sufficiently near one another. Thus, it is also preferred that the members connected at one end to the proximal end of the housing and at the other end to the stop means be bar magnets.

BRIEF DESCRIPTION OF THE DRAWINGS

To facilitate further description of the invention, the following drawings are provided in which:

FIG. 1 is a perspective view of a penis in a flaccid state containing two of the devices of this invention, one in each corpora cavernosa;

FIG. 2 is a perspective view similar to that of FIG. 1 but showing the penis in an erect state due to the activation of the devices;

FIG. 3 is a cross-sectional view taken along line 3—3 of FIG. 2;

FIG. 4 is a side view of a preferred device of this invention;

FIG. 5 shows the device of FIG. 4 implanted in one of the corpora cavernosa and in a less extended/less rigid state;

FIG. 6 is a cross-sectional view taken along line 6—6 of FIG. 5 showing two of the devices implanted in the two corpora cavernosa of the penis;

FIG. 7 shows the two implanted devices being laterally compressed between fingertips;

FIG. 8 shows operation of the two implanted devices to change them from a less rigid to a more rigid configuration, thereby changing the penis from a flaccid state (shown in solid line) to an erect state (shown in phantom line);

FIG. 9 shows the penis and implanted prostheses being manipulated to move coil turns from between the stop means and the proximal ends of the prostheses to between the stop means and the distal ends of the prostheses, thereby to lock the prostheses in the more rigid/more extended configuration;

FIG. 10 shows the devices after a sufficient number of coil turns have been moved towards the distal end of the penis to lock the devices in the more rigid/more extended configuration;

FIG. 11 is a detail view showing an alternate embodiment of the locking or stop means;

FIG. 12 is a cross-sectional view taken along line 12—12 of FIG. 11;

FIG. 13 is a detail view showing an alternate embodiment of the locking or stop means;

FIG. 14 shows another alternate embodiment of the locking or stop means;

FIG. 15 shows yet another alternate embodiment of the locking or stop means;

FIG. 16 is a cross-sectional view taken along line 16—16 of FIG. 15;

FIG. 17 is a view similar to that of FIG. 16 but showing the two adjacent implanted devices being laterally squeezed to unlock the temporary locking means and allow a return to a flaccid state; and FIGS. 18, 19, and 20 show three different well-known surgical approaches for implanting penile prostheses (the penoscrotal, the subcoronal, and the pubic approaches, respectively).

Figure 18:
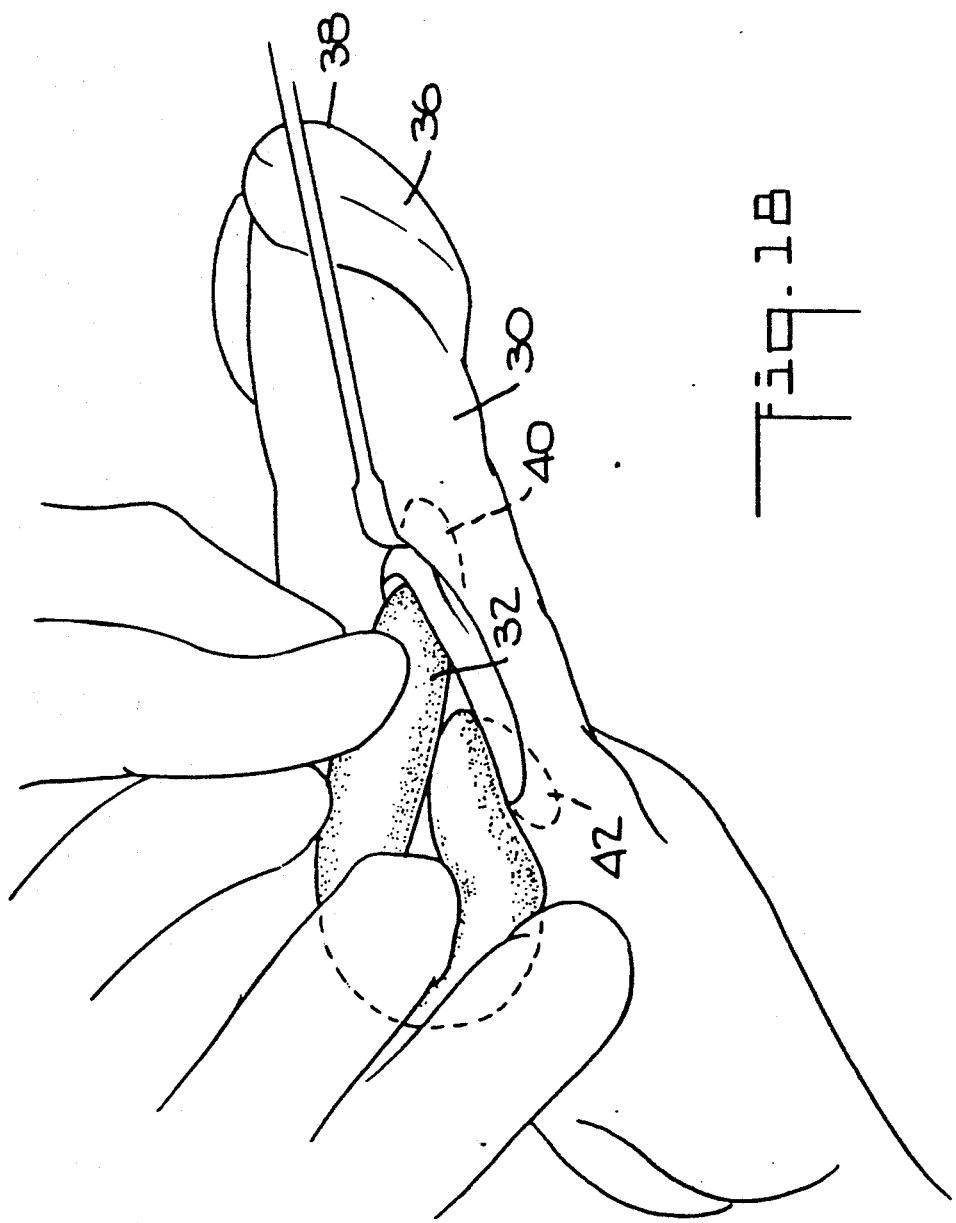

These drawings are provided for illustrative purposes only and should not be used to unduly limit the scope of the invention.

DETAILED DESCRIPTION OF THE INVENTION

In FIG. 1, two devices 32 of this invention are shown implanted in flaccid penis 30 above scrotum 44. Proximal end 42 of each prosthesis is located near symphysis pubis 34. Distal end 40 of each prosthesis points towards distal end 38 of penis 30 and is located within glans 36.

FIG. 2 shows penis 30 in an erect or rigid state due to activation of the two prostheses 32.

FIG. 3 is a cross-sectional view of penis 30, showing each elongate device 32 implanted within corpus cavernosum 50. Also shown are urethra 46, dorsal arteries 48, corpus spongiosum 52, and tunica albuginea 53.

With reference to FIGS. 3 and 4, each prosthesis 32 comprises housing 60 having lateral wall 96, distal end 40, and proximal end 42. Device 32 is implanted within corpus cavernosum 50 so that longitudinal axis 76 of the device corresponds to longitudinal axis 58 of its respective corpus cavernosum.

In the preferred embodiment of FIG. 4, two elongate members 66, which in this case are bar magnets, have their proximal ends fixedly mounted within proximal end 42 of the device. The ends of the bar magnets pointing away from proximal end 42 and towards distal end 40 carry stop means or temporary locking means 64. Because the bar magnets 66 are not totally rigid and because stop means 64 are not fixedly attached to each other or to lateral wall 96 of the housing, stop means 64 are free to move towards and away from longitudinal axis 76 and towards and away from lateral wall 96. Because the two bar magnets 66 have been placed in the housing so that their corresponding magnetic poles (indicated by "S" for south and "N" for north) are immediately adjacent one another, the normal magnetic repulsive force pushes or biases the two north ends of magnets 66 away from each other. That, in turn, biases stop means 64a and 64b, which are attached to the north magnetic ends of the bar magnets, away from each other and away from longitudinal axis 66 and towards lateral wall 96 of housing 60. As will be further discussed below, a lateral compressive force applied perpendicular to the longitudinal axis of the device in the vicinity of stop means 64a and b is sufficient to cause the stop means to move towards one another, thereby moving them towards longitudinal axis 76. That lateral compressive force may be applied at any point along the length of members 66 but is more effective if applied closer to the free (distal) ends of those members.

Coil 54 has numerous coil turns 62. The most distal coil turn 68 lies immediately adjacent distal end 40 of the device and the most proximal coil turn 74 lies immediately adjacent proximal end 42 of the device. Coil turn 72 lies immediately proximal to stop means 64a,b and coil turn 70 lies immediately distal to and abuts the distal faces of stop means 64a,b. As shown in FIG. 3, cross-section 63 of each coil is roughly circular, although, as explained below, any cross-section that allows the coil to perform its required functions may be used. As shown in FIGS. 3 and 4, helical coil 54 has internal longitudinal passageway 56. Because in FIG. 4 the coil turns lying between stop means 64a,b and distal end 40 do not lie immediately adjacent one another, that portion of the device is relatively more flexible and less rigid.

In FIG. 5, device 32 of FIG. 4 is shown implanted in one of the corpora cavernosa of penis 30. Distal end 40 points towards and is located adjacent distal end 51 of corpus cavernosum 50, and proximal end 42 of the prosthesis points towards and is located adjacent proximal end 49 of the corpus cavernosum. Because in FIG. 5 there are not as yet a sufficient number of coil turns between the stop means and the distal end of the device to rigidify that portion of the device, penis 30 is flaccid.

FIG. 6 is a cross-sectional view taken along line 6—6 of FIG. 5 showing two prostheses of this invention lying adjacent one another in the two corpora cavernosa. The two prostheses are identical except that stop means 64a,b of the right-hand device in FIG. 6 are north magnetic poles and stop means 64c,d of the left-hand device are south magnetic poles. The magnetic attraction between the opposite poles of stop means 64b and 64c draws them towards one another, thereby helping to prevent coil turns from passing between those two stop means and the lateral walls of their respective housings 60. At the same time, the repulsive magnetic force between stop means 64a and 64b and the repulsive magnetic force between stop means 64c and 64d also biases the two stop means within each housing away from each other and towards the respective adjacent lateral walls of the housing. Thus, in each device, the two stop means are biased away from the longitudinal center line 76 of that device and towards the respective lateral housing wall, thereby making it more difficult for any coil turns to pass between the stop means and the inner surface of the lateral housing wall.

FIGS. 7 and 8 show fingertips 78 of left hand 86 laterally compressing penis 30, thereby laterally compressing the two corpora cavernosa 50 and thereby laterally compressing the two prostheses implanted therein. As a result of this compression (indicated by arrows 80), coil turns 62 lying between proximal ends 42 of the prostheses and the stop means are partially freed to move past the stop means towards the distal ends of the prostheses. Accordingly, while fingertips 78 of left hand 86 apply the lateral compressive force, right hand 84 is more easily able to move coil turns 62 lying between the stop means and the proximal ends of the devices past the stop means to a position between the stop means and the distal ends of the devices. If the lateral compressive force were not applied, it would be more difficult although not impossible to move those coils towards the distal ends and beyond the stop means.

Arrows 82 in FIG. 8 indicate the direction in which right hand 84 is moved to urge the proximal coil turns past the stop means. As explained below, when a sufficient number of coil turns have been moved distally beyond the stop means, the portion of the prosthesis between the stop means and the distal end is rigidified (and in preferred embodiments lengthened), thereby rigidifying (and in preferred embodiments lengthening) the corpus cavernosum in which the device is located and thereby rigidifying (and in preferred embodiments lengthening) the penis (as shown in phantom line in FIG. 8).

FIG. 9 is a longitudinal view showing the two devices being activated in accordance with FIGS. 7 and 8. Fingertips 78 apply a lateral compressive force while fingertips 79 move in the direction shown by arrows 82 to urge the coil turns past the two stop means 64 in each housing, which have been moved closer to each other, and towards distal ends 40 of the two prostheses.

FIG. 10 shows a sufficient number of coil turns having been moved distally past stop means 64 to lie between stop means 64 and distal ends 40. In FIG. 9, the adjacent coil turns between stop means 64 and distal ends 40 are spaced apart, thereby allowing the two devices, at least in the region between stop means 64 and distal ends 40, to bend easily, resulting in flaccidity. However, when a sufficient number of coil turns have been moved to a position between the stop means and the distal ends of the two devices, coil turns 62 lie immediately adjacent one another, thereby providing increased rigidity to each of the housings and therefore to each of the prostheses and therefore to each of the corpora cavernosa.

That also significantly increases the longitudinal compressive strength of each of the prostheses, thereby further facilitating intercourse. Any longitudinal force applied to the glans and directed generally towards the symphysis pubis (see FIG. 2) will be opposed by each of the prostheses as shown in FIG. 10. Because coil turns 62 lie immediately adjacent one another in FIG. 10, longitudinally directed force applied to distal end 42 is transmitted to most distal coil turn 68 and then to all of the immediately adjacent coil turns 62, including coil turn 70 which lies immediately adjacent the distal surfaces of stop means 64. Because members (bar magnets) 66 are longitudinally incompressible, because their distal ends carry the stop means, and because their proximal ends are fixedly attached to proximal end 42 of each prosthesis, the longitudinal force will then be transmitted through elongate bar magnets 66 to proximal end 42. Thus, each prosthesis will be relatively longitudinally incompressible from distal end 40 to proximal end 42. The circular shape of the coil turns will also make each device laterally rigid, particularly when the coil turns lie immediately adjacent one another (are packed tightly) as in FIG. 10.

FIGS. 11 and 12 show an alternative embodiment of the stop or temporary locking means. In this embodiment, as shown in FIG. 12, three equilaterally spaced bar magnets 64a, 64b, and 64c are used in each device. If two magnets are used (as in the embodiment of FIGS. 4–10) and if axial rotation of either device in its corpus cavernosum should occur, the lateral compressive force (see arrows 80 in FIGS. 7–9) may not result in sufficient movement of the two stop means in a housing towards one another. Use of three evenly spaced stop means as in FIGS. 11 and 12 obviates this potential problem even if such axial rotation of one or both of the devices in their respective corpora cavernosa should occur. Obviously any number of stop means may be used so long as the device can perform its intended function.

FIG. 11 also shows a preferred configuration for each stop means (which configuration is also used in FIGS. 4-10). Specifically, stop means or locking means 64a has a distal face 98 facing the distal end of the device. That surface is in abutting relationship with coil turn 70 which, as explained above, transmits any longitudinal compressive force directed towards the glans through its respective member 66. That surface 98 also pushes coil turn 70 against the other coil turns in the distal part of the device when the coil turns are tightly packed as in FIGS. 10 and 11.

Stop means 64a also has a proximally facing surface 100, which is slanted away from the longitudinal axis of the device. Slanting the proximally directed surfaces facilitates movement of the coil turns lying between the stop means and the proximal end of the device past the stop means. As will be understood by one skilled in the art, as a coil turn lying between the stop means and the proximal end is urged distally (as by hand 84 in FIG. 8), when that coil turn first hits inclined surface 100, further distal movement of that coil turn will urge the respective stop member away from lateral wall 96 of housing 60 and towards the longitudinal axis of the device. Because desirably all of the stop means in a device have such inclined proximally facing surfaces, such distal movement of that coil turn will force all of the stop means inwardly towards the longitudinal axis of the device, thereby allowing that coil turn to move past the stop means into a position between the stop means and the distal end of the device. After that coil turn has moved into such a position, the preferred outward bias of the stop means (as caused by magnetic repulsive force) will urge all of the stop members away from one another and from the longitudinal axis and back towards the lateral wall of the housing. That desirably will bring all of the stop means back into abutting relationship with the lateral wall of the housing and bring distally facing surfaces 98 into a position (as in FIG. 11) where coil turn 70 is temporarily locked between the stop means and the distal end of the device and is unable to be moved towards the proximal end of the device and into a position between the stop means and the proximal end of the device.

FIG. 13 shows an alternative embodiment in which the outward bias (that is, bias away from the longitudinal axis of the housing and towards the lateral wall of the housing) of members 66 and thus of stop means 64 is provided by the inherent resilience of member 66. The two longitudinal arms of member 66 are connected to one another by U-shaped portion 67, which is embedded in proximal end 42 of the device. The material of construction and design of member 66 is such that there is an inherent outward "spring" to the two arms of the member. Alternatively, a spring or other resilient member (e.g., an elastomeric ball) could be mounted between the two arms of member 66 to bias them outwardly.

In FIG. 14, a single unitary member 66 has its proximal end 88 embedded in proximal end 42 of the housing. Distal end 90 of member 66 has connected to it two sloping stop means 64. Coil turns located between the stop means and the proximal end of the device may be slid past the stop means to a position between the stop means and the distal end of the device as in the other embodiments. The slope of the distal faces of stop means 64 helps to prevent coil turns located between the stop means and the distal end from being forced by a longitudinal compressive force past the stop means to a position between the stop means and the proximal end. Specifically, when a longitudinal compressive force directed proximally is applied to the distal end of the device, it is transmitted through the coil turns lying adjacent one another (as in FIG. 10) to coil turn 70. However, because of the slope of the distal faces of stop means 64 in FIG. 14, further compressive force tends to force coil turn 70 to laterally compress, that is, become smaller in diameter, as it is forced downward towards the "valley" where the distal faces of stop members 64 on the same member 66 meet one another. That tends to reduce the possibility that such longitudinal compressive force on the device will be able to cause coil turn 70 resting on the distal faces of the stop means to slide between the lateral edges of the stop means and lateral wall 96 of the housing.

In the other embodiments shown herein, the distal surfaces of the stop members are roughly perpendicular to the longitudinal axis of the housing. Thus, for example, in FIG. 13, lateral compressive force applied to the sides of the penis and therefore to the sides of the housing forces the stop members together in a direction generally perpendicular to the longitudinal axis and allows the coil turns to be moved proximally or distally between the stop means and the lateral wall of the housing. However, in the embodiment of FIG. 14, lateral compressive force tends to cause the ends of the two stop means in each housing to move distally. That provides the required clearance between the ends of the stop means and the lateral wall of the housing to allow the coil turns to be moved distally or proximally.

FIGS. 15, 16, and 17 show alternative stop means 64a,b,c, and d for the two devices. Stop means 64a and 64b are cantilevered tabs attached to cylindrical liner or sleeve 102, which is located in the proximal portion of the housing. In the embodiment of, for example, FIG. 7, lateral compressive force (arrows 80) moves stop means 64a towards stop means 64b and stop means 64d towards stop means 64c. In contrast, lateral compression of the devices of FIGS. 15-17 (arrows 80 in FIG. 17) does not move the two stop means in each housing together. Instead, as seen in the left-hand device of FIG. 17, lateral compression applied by fingertips 78 causes gap 104 to form between coil turn 72 and sleeve 102. A similar gap (not indicated by reference numeral) forms in the right-hand device of FIG. 17. Those gaps and manipulation of the two devices enables coil turns to be moved from a location between the stop means and the distal portions of the devices, past the stop means, to a location between the stop means and the proximal ends of the devices so that the devices can be changed from their activated configuration of FIGS. 15 and 16 to a deactivated configuration.

As with the other embodiments, when the lateral force is no longer applied, the stop means move back to their normal positions to temporarily lock all of the coil turns between the stop means and the distal end of the device in that position. If a sufficient number of coil turns have been moved to the distal portion of the device (that is, to a position between the stop means and the distal end of the device), sufficient rigidity will be imparted to the device, which will then impart sufficient rigidity to the corpus cavernosum in which that device is located. In FIG. 17, when the lateral compressive force represented by arrows 80 is no longer applied, gap 104 between coil turn 72 and sleeve 102 will disappear. As is evident from comparing FIGS. 16 and 17, each gap results from the housing wall being relatively more flexible and plastic laterally than the coil, thereby allowing the housing wall to deform laterally more than the adjacent coil turn. FIGS. 16 and 17 show that the housing walls (and to a smaller extent, the adjacent coil turns) are deformed from essentially circular cross-sections to elliptical cross-sections by the lateral compressive force applied by fingertips 78.

FIG. 18 shows a device of this invention being implanted during surgery using the penoscrotal approach. The incision has been made and the flexibility of the present device allows proximal end 42 and distal end 40 to be placed into the corpus cavernosum. The device will be further inserted into the corpus and the incision will be closed in the known manner. A second similar device will be placed in the other corpus cavernosum (not shown).

Figure 19:
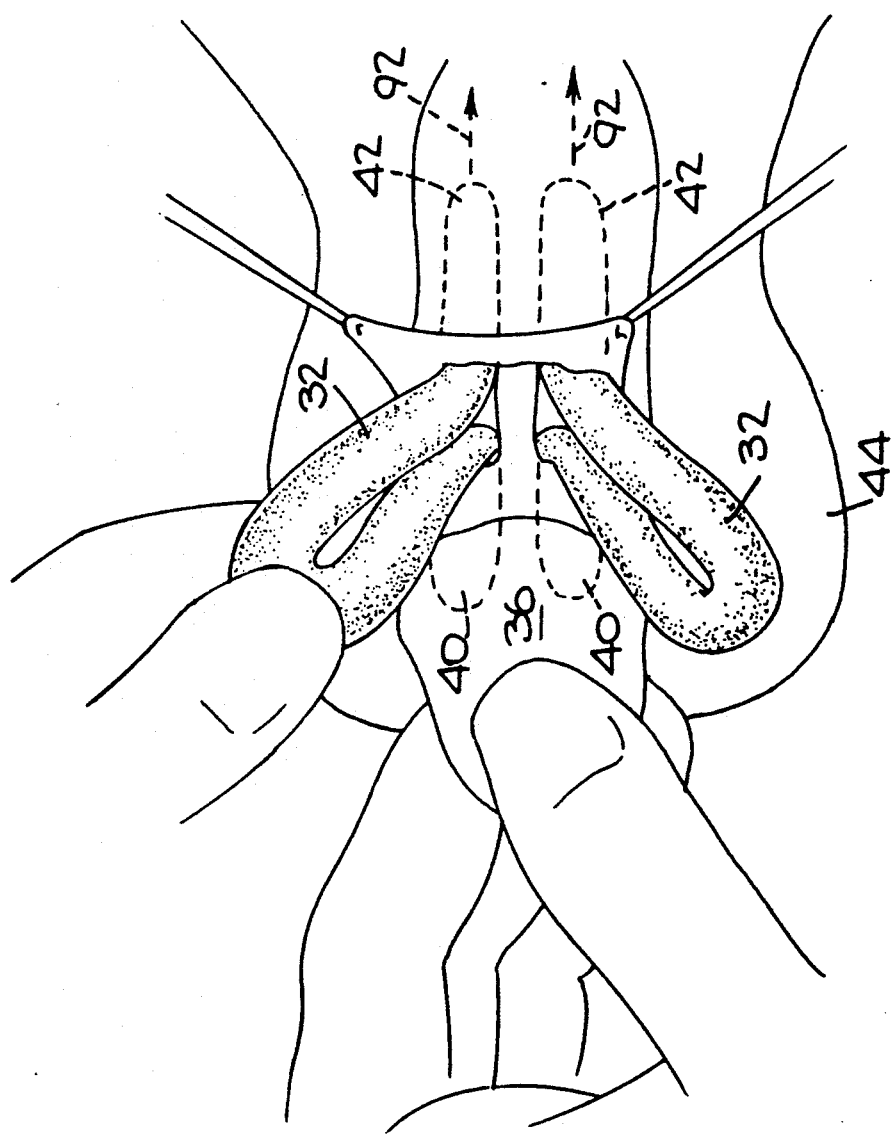

FIG. 19 shows two devices of this invention being placed in the corpora cavernosa during surgery in accordance with the subcoronal approach. Proximal ends 42 will be pushed in the directions shown by arrows 92 to occupy the rest of the corpora cavernosa. Distal ends 40 of the two devices have already been placed in the corpora so that the distal ends of the devices lie adjacent the distal ends of the corpora.

FIG. 20 shows two devices of this invention being implanted during surgery in accordance with the pubic approach. The proximal ends 42 of the two devices lie adjacent the proximal ends of the two corpora cavernosa. The two devices will be further pushed into the corpora so that their distal ends 40 move distally in the directions shown by arrows 94 towards glans 36. In embodiments of this invention in which the proximal region of the device (between the stop means and the distal end) is relatively less flexible, the subcoronal (FIG. 19) and pubic (FIG. 20) approaches may be more desirable than the penoscrotal (FIG. 18) approach.

As will be understood by one skilled in the art, the design of, materials of construction of, and implantation techniques for the devices of this invention are not critical so long as the devices can perform their intended function in accordance with the teachings herein. Any materials of construction may be used so long as they allow the devices to have a satisfactorily long and useful life after implantation and allow the devices to perform their intended function. Generally, physiologically inert (non-reactive, non-toxic, etc.) materials will be used. For example, the housing may be made of polytetrafluoroethylene coated with silicone rubber or polysulfone. Use of a physiologically inert material prevents fixation of the device by the "biofilm" that typically develops with implanted devices not having such an outer covering.

The coil should be made of a material having sufficient toughness, durability, strength, and memory so that the coil remains helically shaped, can not be permanently laterally or longitudinally deformed to any significant extent, and can be moved without difficulty past the stop means when coil turns are being moved distally or proximally during activation or deactivation. The coil may be made of metallic or of non-metallic material, for example, it may be a silicon memory coil. The cross-section of the coil (when viewed longitudinally) is most preferably circular (because of the anatomy of the corpora cavernosa), although other curved shapes may be used. The cross-section of the coil turn (perpendicular to the helical path of the coil) may be of any size or shape that allows the coil to perform its intended function. In FIG. 3, for example, coil turn cross-section 63 is roughly circular. Other shapes may be used. For example, the cross-section may be rectangular so that the coil turn is relatively flat. Such a shape allows for better stacking of the coil turns and tends to prevent adjacent turns from sliding laterally on one another when the coil turns are tightly stacked in the activated configuration (as in FIG. 10). That imparts increased lateral rigidity to the device.

The devices should be sufficiently anchored and stable within the corpora so that longitudinal proximately directed compressive forces (as, for example, during thrusting) are transmitted through the essentially longitudinally incompressible device (after activation) to the body of the user. Although the distal and proximal ends of the embodiments of the drawings are shown having essentially the same size and shape, as will be understood by one skilled in the art, the distal end of the device may be bullet-, cone-, or parabolically shaped. The root or proximal end of the device of this invention need not have that shape and may have any anatomically satisfactory shape that allows it to be implanted and sufficiently anchored in the proximal end of its corpus cavernosum.

As explained above, a sufficient number of coil turns must be moved distally beyond the stop means so that the distal portion of the device (between the stop means and the distal end of the device) has been sufficiently rigidified to make the entire device sufficiently rigid to allow intercourse. The device, including the stop means and coil turns, must be designed to allow easy and simple deactivation of the device (for returning to the flaccid state), that is, to allow coil turns to be moved proximally from a position between the stop means and the distal end of the device to a position between the stop means and the proximal end of the device.

By moving a sufficient number of coil turns distally to a location between the stop means and the distal end of the device, sufficient lateral rigidity and longitudinal incompressibility of the device can be achieved. Generally, at least one coil turn, usually at least two coil turns, desirably at least three coil turns, preferably at least five coil turns, more preferably at least seven coil turns, and most preferably at least ten coil turns will be moved distally for activation. Higher numbers of coil turns will be moved in preferred embodiments where the device not only is rigidified during activation but is also significantly lengthened.

In preferred embodiments, the housing itself is elongatable, such elongation occurring as more coil turns are moved to the distal portion of the device. Such lengthening of the device (and, therefore, of the corpus cavernosum) may be accomplished in several ways. First, the lateral wall of the housing may be elastic and resilient to allow the lateral wall to be longitudinally stretched as more and more coil turns are moved to a location between the stop means and the distal end of the device. Obviously in this case the material of construction of the housing wall must allow the wall to longitudinally stretch during activation but also have sufficient resilience and memory so that the wall shortens longitudinally during deactivation (movement of coil turns from the distal portion of the device to a location between the stop means and the proximal end of the device). Such lengthening and shortening of the housing wall is indicated by segment lines 61a and 61b in FIG. 4.

Alternatively, the housing wall may normally be folded in on itself if the housing wall material is not sufficiently elongatable. That allows the housing to increase in length without the need for significant stretching of the housing wall material to occur. With such a configuration, the housing wall of a device would be longer than is needed when the penis is flaccid. The additional length of housing material would merely reside in the respective corpus cavernosum until activation and elongation of the device occurred. Means may also be incorporated into the device to retract any additional length of housing wall not needed when the device is in a deactivated (non-elongated) state. The housing wall may be reinforced, for example, by cylindrical bands, to increase its hoop strength.

Surgery to implant the devices of this invention may proceed according to any standard technique now known or later developed. Perioperative antibiotics are used for prophylaxis. Any incision may be used (for example, infrapubic, penile, scrotal, and perineal). Corporotomies may be made in the usual manner. The prosthesis of this invention is placed in its respective corpus after dilation and sizing using any known or later-developed technique. The incision layers may be closed in standard fashion.

Because at least the distal portion of the device when in the deactivated state is highly flexible, it is maneuverable through acute angles and, accordingly, smaller corporotomies for implantation may be sufficient. That in turn reduces the opportunity for erosion secondary to corporal dehiscence. Furthermore, less time is needed to close such smaller corporotomies.

The proximal portion of the device should be long enough so that the stop means or temporary locking means are located just beyond the penoscrotal junction to allow easy accessibility for manual compression and release of the temporary locking or stop means for activation and deactivation. Typically, the proximal portion of the device will be approximately 6–8 centimeters long. The distal portion of the device will typically be 9–11 centimeters long, and the outer diameter of the housing will typically be 10–15 millimeters.

In contrast to known devices (except for the oldest devices, which were rigid, non-bendable rods or bars), the prosthesis of this invention is simpler and has no intricate moving parts or supporting cables or pumps or valves, any of which may fail during use. There is also no fluid to leak. In preferred embodiments in which repulsive magnetic force is used to bias the stop means to temporarily lock coil turns in the distal portion of the device, it is less likely that those parts (for example, bar magnets 66) will suffer material fatigue and resulting failure. If for some reason such magnets no longer have sufficient magnetic repulsive force, they may be re-magnetized using external means. However, the magnets used are permanent magnets and would be expected to retain their magnetic properties throughout the patient's lifetime. Such external re-magnetization (by induction) obviates the need for open surgical correction.

In the unlikely event that sufficient rigidity can not be obtained with this device by moving coil turns distally beyond the stop means, a constriction ring may be used in the known manner by placing it at the base of the penis.

Sizing is also facilitated and simplified by the present invention. The activated length is determined by the number of coil turns located between the stop means and the distal end of the device. Accordingly, a wide range of activated sizes can be accommodated by a single standard size device because only as many coil turns as are needed for the maximum allowable elongation in any particular case need be moved distally beyond the stop means to a position between the stop means and the distal end. The coil turns that need not be moved to the distal portion of the device will remain in the proximal portion (i.e., between the stop means and the proximal end). Hence, in the operating room, prosthesis selection is simpler, fewer different size devices need be stocked or manufactured, and production costs are thereby reduced.

Variations and modification will be apparent to those skilled in the art and the claims are intended to cover all variations and modifications falling within the true spirit and scope of the invention.

I claim:

1. A penile prosthesis implantable in a person having a symphysis pubis and a penis, the penis having a corpus cavernosum, which prosthesis is changeable from a less rigid configuration to a more rigid configuration, which is temporarily lockable in the more rigid configuration, and which is adapted to be located in the corpus cavernosum and which in the more rigid configuration helps to maintain the corpus cavernosum and the penis in a more rigid configuration; the corpus cavernosum having a proximal end, which is nearer the symphysis pubis, and a distal end, which is farther from the symphysis pubis; said prosthesis comprising:

(a) a flexible elongate housing having a lateral wall, a longitudinal axis, a proximal end, and a distal end, the proximal end of the housing being adapted to be located closer to the proximal end of the corpus cavernosum and the distal end of the housing being adapted to be located closer to the distal end of the corpus cavernosum;

(b) an elongate coil inside the housing and comprising a plurality of turns, the coil having a distal end and a proximal end, the distal end of the coil being located toward the distal end of the housing and the proximal end of the coil being located toward the proximal end of the housing;

(c) locking means located between the distal and proximal ends of the housing, at least some of said plurality of coil turns normally being located between the proximal end of the housing and the locking means in the less rigid configuration, the locking means comprising (i) means for permitting at least one of the coil turns located between the proximal end of the housing and the locking means to be moved to a location between the locking means and the distal end of the housing and (ii) means for temporarily locking the coil turns located between the locking means and the distal end of the housing so that they cannot be moved back to their normal location between the proximal end of the housing and the locking means so long as the locking means is locked;

the coil, locking means, and housing being designed so that moving a sufficient number of coil turns from their normal location between the locking means and the proximal end of the housing to a position between the locking means and the distal end of the housing and locking them in said position locks the housing in a more rigid configuration, thereby temporarily locking the prosthesis in a more rigid configuration and thereby locking the corpus cavernosum and penis in a more rigid configuration.

2. The prosthesis of claim 1 in which the locking means comprises at least one locking member that is movable towards and away from the longitudinal axis of the housing.

3. The prosthesis of claim 2 having at least two locking members.

4. The prosthesis of claim 3 wherein the at least two locking members are normally biased away from the longitudinal axis of the housing by a biasing force.

5. The prosthesis of claim 4 further comprising magnetic biasing means, which supplies a magnetic biasing force.

6. The prosthesis of claim 4 further comprising deformable and resilient biasing means, which supplies the biasing force.

7. The prosthesis of claim 2 further comprising an elongate member having first and second ends, the first end being connected to the proximal end of the housing and the locking member being connected to the second end of the elongate member.

8. The prosthesis of claim 7 comprising a plurality of locking members that are connected to the elongate member.

9. The prosthesis of claim 7 comprising a plurality of locking members and a plurality of elongate members whose first ends are connected to the proximal end of the housing and whose second ends are each connected to a different one of the locking members.

10. The prosthesis of claim 9 wherein the second ends of the plurality of locking members are normally biased away from the longitudinal axis of the housing and from each other by a biasing force.

11. The prosthesis of claim 10 further comprising magnetic biasing means, which supplies a magnetic biasing force.

12. The prosthesis of claim 11 wherein the elongate members are bar magnets.

13. The prosthesis of claim 10 further comprising deformable and resilient biasing means, which supplies the biasing force.

14. The prosthesis of claim 2 wherein the at least one locking member has a first surface facing towards the proximal end of the coil that is inclined so that a point on the first surface is farther from the proximal end of the coil the closer that point on the surface is to the lateral wall of the housing and a second surface facing towards the distal end of the coil that is roughly perpendicular to the longitudinal axis of the housing, which second surface is adapted to contact the adjacent coil turn to temporarily lock it in place.

15. The prosthesis of claim 1 wherein the housing is elongatable.

16. A manually operable penile prosthesis implantable in a person having a symphysis pubis and a penis, the penis having a corpus cavernosum, which prosthesis is elongatable from a less extended configuration to a more extended configuration, which is temporarily lockable in the more extended configuration, and which is adapted to be located in the corpus cavernosum and which in the more extended configuration helps to maintain the corpus cavernosum and the penis in a more extended configuration; the corpus cavernosum having a proximal end, which is nearer the symphysis pubis, and a distal end, which is farther from the symphysis pubis; said prosthesis comprising:

(a) an elongatable housing having a lateral wall, a longitudinal axis, a proximal end, and a distal end, the proximal end of the housing being adapted to be located closer to the proximal end of the corpus cavernosum and the distal end of the housing being adapted to be located closer to the distal end of the corpus cavernosum;

(b) an elongate coil inside the housing and comprising a plurality of turns, the coil having a distal end and a proximal end, the distal end of the coil being located toward the distal end of the housing and the proximal end of the coil being located toward the proximal end of the housing;

(c) manually operable locking means located between the distal and proximal ends of the housing, at lest some of said plurality of coil turns normally being located between the proximal end of the housing and the locking means in the less extended configuration, the locking means comprising (i) means for permitting at least one of the coil turns located between the proximal end of the housing and the locking means to be manually moved to a location between the locking means and the distal end of the housing and (ii) means for temporarily locking the coil turns located between the locking means and the distal end of the housing so that they cannot be moved back to their normal location between the proximal end of the housing and the locking means so long as the locking means is locked;

the coil, locking means, and housing being designed so that moving a sufficient number of coil turns from their normal location between the locking means and the proximal end of the housing to a position between the locking means and the distal end of the housing and locking them in said position locks the housing in a more extended configuration, thereby temporarily locking the prosthesis in a more extended configuration and thereby locking the corpus cavernosum and penis in a more extended configuration.

17. The prosthesis of claim 16 in which the locking means comprises at least one locking member that is manually movable towards and away from the longitudinal axis of the housing.

18. The prosthesis of claim 17 having at least two locking members.

19. The prosthesis of claim 18 wherein the at least two locking members are normally biased away from the longitudinal axis of the housing by a biasing force.

20. The prosthesis of claim 19 further comprising magnetic biasing means, which supplies a magnetic biasing force.

21. The prosthesis of claim 19 further comprising formable and resilient biasing means, which supplies the biasing force.

22. A manually operable penile prosthesis implantable in a person having a symphysis pubis and a penis, the penis having a corpus cavernosum, which prosthesis is elongatable from a less extended configuration to a more extended configuration, which is temporarily lockable in the more extended configuration, and which is adapted to be located in the corpus cavernosum and which in the more extended configuration helps to maintain the corpus cavernosum and the penis in a more extended configuration; the corpus cavernosum having a proximal end, which is nearer the symphysis pubis, and a distal end, which is farther from the symphysis pubis; said prosthesis comprising:

(a) an elongate elongatable housing having a lateral wall, a longitudinal axis, a proximal end, and a distal end, the proximal end of the housing being adapted to be located closer to the proximal end of the corpus cavernosum and the distal end of the housing being adapted to be located closer to the distal end of the corpus cavernosum;

(b) an elongate coil inside the housing and comprising a plurality of turns, the coil having a distal end and a proximal end, the distal end of the coil being located toward the distal end of the housing and the proximal end of the coil being located toward the proximal end of the housing, the turns of the coil also defining an elongate passageway centrally located in the coil and having a longitudinal axis, the longitudinal axis of the passageway roughly corresponding to the longitudinal axis of the housing;

(c) manually operable locking means located between the distal and proximal ends of the housing, at lest some of said plurality of coil turns normally being located between the proximal end of the housing and the locking means in the less extended configuration, the locking means comprising (i) means for permitting at least one of the coil turns located between the proximal end of the housing and the locking means to be manually moved to a location between the locking means and the distal end of the housing and (ii) means so long as the temporary locking means is locked;

the coil, locking means, and housing being designed so that moving a sufficient number of coil turns from their normal location between the locking means and the proximal end of the housing to a position between the locking means and the distal end of the hosing and locking them in said position locks the housing in a more extended configuration, thereby temporarily locking the prosthesis in a more extended configuration and thereby locking the corpus cavernosum and penis in a more extended configuration.

23. The prosthesis of claim 22 in which the locking means comprises at least one locking member that is movable towards and away from the longitudinal axis of the passageway.

24. The prosthesis of claim 23 having at least two locking members.

25. The prosthesis of claim 24 wherein the at least two locking members are normally biased away from the longitudinal axis of the passageway by a biasing force.

26. The prosthesis of claim 25 further comprising magnetic biasing means, which supplies a magnetic biasing force.

27. The prosthesis of claim 25 further comprising deformable and resilient biasing means, which supplies the biasing force.

28. The prosthesis of claim 23 further comprising an elongate member having first and second ends, the first end being connected to the proximal end of the housing and the locking member being connected to the second end of the elongate member.

29. The prosthesis of claim 28 comprising a plurality of locking members that are connected to the elongate member.

30. The prosthesis of claim 28 comprising a plurality of locking members and a plurality of elongate members whose first ends are connected to the proximal end of the housing and whose second ends are each connected to a different one of the locking members.

31. The prosthesis of claim 30 wherein the plurality of locking members are normally biased away from the longitudinal axis of the passageway and from each other by a biasing force.

32. The prosthesis of claim 31 further comprising magnetic biasing means, which supplies a magnetic biasing force.

33. The prosthesis of claim 32 wherein the elongate members are bar magnets.

34. The prosthesis of claim 31 further comprising deformable and resilient biasing means, which supplies the biasing force.

35. The prosthesis of claim 28 wherein the elongate member is located substantially within the passageway of the coil.

36. The prosthesis of claim 23 wherein the at least one locking member has a first surface facing towards the proximal end of the coil that is inclined so that a point on the first surface is farther from the proximal end of the coil the closer that point on the surface is to the lateral wall of the housing.

37. The prosthesis of claim 23 wherein the at least one locking member has a second surface facing towards the distal end of the coil that is roughly perpendicular to the longitudinal axis of the coil, which second surface is adapted to contact the adjacent coil turn to temporarily lock it in place.

38. A manually operable penile prosthesis implantable in a person having a symphysis pubis and a penis, the penis having a corpus cavernosum, which prosthesis is elongatable from a less extended configuration to a more extended configuration, which is temporarily lockable in the more extended configuration, and which is adapted to be located in the corpos cavernosum and which in the more extended configuration helps to maintain the corpus cavernosum and the penis in a more extended configuration; the corpus cavernosum having a proximal end, which is nearer the symphysis pubis, and a distal end, which is farther from the symphysis pubis; said prosthesis comprising:

(a) an elongate elongatable housing having a lateral wall, a longitudinal axis, a proximal end, an a distal end, the proximal ned of the housing being adapted to be located closer to the proximal end of the corpus cavernosum and the distal end of the housing being adapted to be located closer to the distal end of the corpus cavernosum;

(b) an elongate coil inside the housing and comprising a plurality of turns, the coil having a distal end and a proximal end, the distal end of the coil being located toward the distal end of the housing and the proximal end of the coil being located toward the proximal end of the housing, the turns of the coil also defining an elongate passageway centrally located in the coil and having a longitudinal axis, the longitudinal axis of the passageway roughly corresponding to the longitudinal axis of the housing;

(c) a plurality of members in the housing, each member having a proximal end and a distal end, the members being located at least partially within the elongate passageway of the coil and being shorter than the elongate passageway, the proximal ends of the members being closer to the proximal end of the housing and the distal ends of the members being farther from the proximal end of the housing, the distal ends of the members being laterally movable towards and away from each other, at lest some of said plurality of coil turns normally being located between the proximal end of the housing and the distal ends of the members in the less extended configuration;

(d) stop means connected to the members near the distal ends of the members so that the step means are movable laterally towards and away from each other, the step means being normally biased away from each other towards the lateral wall of the housing to temporarily lock the coil turns located between the distal ends of the members and the distal end of the housing so that they cannot be moved back to their normal location between the proximal end of the housing and the distal ends of the members, the stop means being sufficiently manually movable towards each other to permit at lest one of the plurality of coil turns located between the proximal end of the housing and the distal ends of the members to be manually moved to a location between the distal ends of the members and the distal ends of the housing;

the coil members, stop means, and housing being designed so that moving a sufficient number of coil turns from their normal location between the distal ends of the members and the proximal end of the hosing to a position between the distal ends of the members and the distal end of the housing and locking them in said position locks the housing in a more extended configuration, thereby temporarily locking the prosthesis in a more extended configuration nd thereby locking the corpus cavernosum and penis in a more extended configuration.

39. The prosthesis of claim 38 wherein the step means are located at the distal ends of the members.

40. The prosthesis of claim 38 wherein the stop means are normally biased away from each other by magnetic force.

41. The prosthesis of claim 40 wherein the members are bar magnets and they are arranged to have their corresponding magnetic poles adjacent one another.

42. The prosthesis of claim 41 wherein the stop means are located at the distal ends of the members.

43. The prosthesis of claim 38 wherein there is one stop means at the end of each member and each stop means has a first surface facing towards the proximal end of the coil that is inclined so that a point on the first surface is farther from the proximal end of the coil the closer that point on the surface is to the lateral wall of the housing.

44. The prosthesis of claim 43 wherein each stop means has a second surface facing towards the distal end of the coil that is roughly perpendicular to the longitudinal axis of the coil, which second surface is adapted to contact the adjacent coil turn to temporarily lock it in place.

* * * * *

UNITED STATES PATENT AND TRADEMARK OFFICE
CERTIFICATE OF CORRECTION

PATENT NO. : 5,230,694

DATED : July 27, 1993

INVENTOR(S) : JEFFREY L. ROSENBLUM

It is certified that error appears in the above-indentified patent and that said Letters Patent is hereby corrected as shown below:

Column 18, line 15: "lest" should read --least--.

Column 18, line 54: "formable" should read --deformable--.

Column 19, line 20: "lest" should read --least--;

Column 19, line 29: after "means" and before "so" insert --for temporarily locking the coil turns located between the locking means and the distal end of the housing so that they cannot be moved back to their normal location between the proximal end of the housing and the locking means--.

Column 21, line 2: "lest" should read --least--;

Column 21, line 8: "step" should read --stop--;

Column 21, line 10: "step" should read --stop--;

Column 21, line 19: "lest" should read --least--;

Column 21, line 28: "hosing" should read --housing--;

Column 22, line 4: "nd" should read --and--.

UNITED STATES PATENT AND TRADEMARK OFFICE
CERTIFICATE OF CORRECTION

PATENT NO. : 5,230,694

DATED : July 27, 1993

INVENTOR(S) : JEFFREY L. ROSENBLUM

It is certified that error appears in the above-indentified patent and that said Letters Patent is hereby corrected as shown below:

Column 22, line 6:  "step" should read --stop--.

Signed and Sealed this

Twenty-ninth Day of March, 1994

Attest:

BRUCE LEHMAN

*Attesting Officer*  *Commissioner of Patents and Trademarks*